United States Patent [19]

Hofinger et al.

[11] Patent Number: 4,781,918
[45] Date of Patent: Nov. 1, 1988

[54] COSMETIC AGENTS FOR HAIR AND SKIN TREATMENT

[75] Inventors: Manfred Hofinger, Burgkirchen; Alwin Reng, Kelkheim; Jochen M. Quack, Eppstein/Taunus, all of Fed. Rep. of Germany

[73] Assignee: Hoechst Aktiengesellschaft, Frankfurt am Main, Fed. Rep. of Germany

[21] Appl. No.: 106,058

[22] Filed: Oct. 7, 1987

[30] Foreign Application Priority Data

Oct. 9, 1986 [DE] Fed. Rep. of Germany ....... 3634417

[51] Int. Cl.$^4$ .......................... A61K 7/06; A61K 7/09
[52] U.S. Cl. ......................................... 424/70; 424/71
[58] Field of Search .................................... 424/70, 71

[56] References Cited

U.S. PATENT DOCUMENTS

| | | | |
|---|---|---|---|
| 3,740,421 | 6/1973 | Schmolka | 424/70 |
| 4,369,037 | 1/1983 | Matsunaga et al. | 424/70 |
| 4,702,906 | 10/1987 | Jacquet et al. | 424/70 |

FOREIGN PATENT DOCUMENTS

| | | | |
|---|---|---|---|
| 0056412 | 4/1982 | Japan | 424/70 |
| 0216112 | 12/1983 | Japan | 424/70 |

Primary Examiner—John E. Kittle
Assistant Examiner—P. J. Ryan

[57] ABSTRACT

An agent for treatment of hair and skin, containing a quarternary ammonium compound of the formula

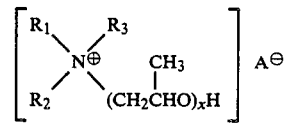

in which $R_1$ and $R_2$ may be identical or different and denote $C_8$–$C_{22}$-alkyl or $C_8$–$C_{22}$-alkenyl, $R_3$ denotes $C_1$–$C_3$-alkyl, x denotes a number from 1 to 3, and $A^\ominus$ denotes the anion of $C_2$–$C_6$-carboxylic acid, which may contain 1 to 3 hydroxyl groups, or the hydrogen phosphate anion.

8 Claims, No Drawings

COSMETIC AGENTS FOR HAIR AND SKIN TREATMENT

DESCRIPTION

Human hair is damaged by changing exogenic influences. Damage to the hair structure can take place physically, for example through combing, brushing and back-combing, or during hair washing. Further damage is observed on bleaching, coloring or perming. Microbiological influences can also adversely affect the hair structure. In order to minimize these influences, it is usual to use hair-treatment agents in the form of hair rinses or conditioners. In addition, the combability of wet and dry hair is substantially improved and, at the same time, static charge is decreased when these preparations are used. These cosmetic agents for hair treatment can be used in aqueous or aqueousalcoholic solution or in the form of emulsions and/or suspensions.

It is known that cationic compounds, generally quarternary ammonium compounds, are highly suitable for the preparation of such cosmetic agents for hair treatment. These surfactants have a high substantivity to hair, and the mono- or multimolecular film produced gives the cosmetic properties desired. The cationic surfactants most used for the preparation of hair-treatment agents belong to the group comprising the alkyltrimethylammonium chlorides or bromides, the dialkyldimethylammonium chlorides or the alkyldimethylbenzylammonium chlorides.

In addition, water-soluble, cationic polymers are also employed, alone or together with the abovementioned quarternary ammonium compounds.

However, the majority of these cationic surfactants used have a number of disadvantages, such as, for example, too poor combability of wet hair, build-up or accumulation on the hair, unfavorable dermatological or toxicological properties and formulation problems, i.e. insufficient increase in consistency.

Surprisingly, it has now been found that agents which do not have these disadvantages can be prepared using the oxypropylated quarternary ammonium compounds shown below. The invention therefore relates to agents for treatment of hair and also for skin containing a quarternary ammonium compound of the formula

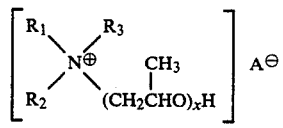

in which $R_1$ and $R_2$ may be identical or different and denote $C_8$–$C_{22}$-alkyl or $C_8$–$C_{22}$-alkenyl, $R_3$ denotes $C_1$–$C_3$ alkyl, x denotes a number from 1 to 3 and $A^\ominus$ denotes the anion of a $C_2$–$C_6$-carboxylic acid which may contain 1 to 3 hydroxyl groups, or the hydrogen phosphate anion.

In a preferred fashion $R_1$ and $R_2$ denote $C_{12}$–$C_{18}$-alkyl, $R_3$ denotes methyl, x denotes a number from 1.5 to 2.5, and $A^\ominus$ denotes the anion of lactic acid, citric acid or tartaric acid. The quarternary ammonium compounds of the formula above can be prepared analogously to the process described in U.S. Pat. No. 4,409,109.

Using these oxypropylated quarternary ammonium compounds, agents for treatment of hair can be prepared which, besides these, contain the components which are conventionally used, such as thickeners, fat components, preservatives, perfume oils, colorants, light screens and other cosmetic active compounds, emulsified or dispersed in water or dissolved in alcohols. The quarternary ammonium compounds described have the following advantages when used in conditioning hair rinses, hair fixatives or wave sets.

1. Improvement in wet combability

Combability of wet hair is tested invivo on at least 6 test subjects having, if possible, previously damaged hair.

The test is carried out by washing the hair of the test subjects twice in a usual fashion under standardized conditions and subsequently drying gently. The hair of the subjects is parted in the center of the head and treated in each case with 10 ml of an aqueous solution containing the quarternary ammonium compounds in a concentration of 0.1%. The solution is allowed to act for 5 minutes at room temperature. The hair is subsequently rinsed for 2 minutes with hand-hot tap water, and, in accordance with practice, the excess of water is removed from the hair using hand towels. Using 2 identical combs, the sides to be compared are combed synchronously and the resistance which occurs is determined. It was shown that, when using the substances according to the invention, very good combability of wet human hair is produced compared to commercially available quarternary ammonium compounds.

The combability of subsequently dried hair is also very good. The same applies to the so-called styling properties of the hair (see table 1)

TABLE 1

|  | Combability | | | |
|---|---|---|---|---|
|  | Wet hair | Dry hair | Antistatic behavior | Feel of the hair |
| Cetyltrimethylammonium chloride (comparison) | 3 | 3 | 4 | 2 |
| Stearyldimethylbenzyl-ammonium chloride (comparison) | 2 | 3 | 2 | 3 |
| Distearylmethylpoly-(oxypropyl)ammonium lactate (according to the invention) | 4 | 4 | 3–4 | 4 |
| Without quarternary ammonium | 0 | 1 | 1 | 1 |

4 = very good
3 = good
2 = moderate
1 = poor
0 = very poor

2. Foaming behavior during use

A further advantage of oxypropylated quarternary ammonium compounds is their freedom from foaming in aqueous dilution. This is of particular advantage when used in hair conditioners, since considerable foam formation gives the consumer the impression of the presence of residual amounts of shampoo, which in turn leads to time-consuming and annoying increased rinsing out of the hair treatment after its use. When the oxypropylated quarternary ammonium compounds are used, no foaming action is observed, in contrast to the cetyltrimethylammonium chloride which is usually used in practice.

The foaming behavior can also be determined in vitro using the so-called foam-beating method in accordance with DIN 53 902. An aqueous solution containing 0.1% of the active substance and having a water hardness of 356 ppm of $CaCO_3$ is beaten 25 times at 20° C. under standardized conditions. The volume of foam produced in a cetyltrimethylammonium chloride solution in this test is 740 cm$^3$ whereas the oxypropylated quarternary ammonium compounds exhibit no foaming action.

3. Simple formulation

The preferred form of hair-treatment agents is a dispersion containing the quarternary ammonium compounds and additional thickeners, such as, for example, cetyl alcohol and/or stearyl alcohol. Through the use of these thickeners, a practical viscosity is achieved which, on the one hand, simplifies measuring out and, on the other hand, makes possible a better distribution on the hair. The incorporation of these substances is technologically complicated and the final viscosity in some cases only reaches a maximum after a relatively long time.

In the case of the oxypropylated quarternary ammonium compounds according to the invention, it has been found that it is possible to produce medium to high-viscosity hair rinses without additional thickeners being necessary. For example, the following viscosities were measured as a function of the concentration at 20° C. using a Brookfield viscometer:

| | |
|---|---|
| 1% of active substance dissolved in water: | 1140 mPas |
| 2% of active substance dissolved in water: | 2050 mPas |
| 3% of active substance dissolved in water: | 2180 mPas |
| 5% of active substance dissolved in water: | 2810 mPas |

The oxypropylated quarternary ammonium compounds to be used according to the invention can be incorporated into the hair rinses in a fashion which is known per se. In these, 0.5–10% of the oxypropylated quarternary ammonium compounds alone or in combination with other quarternary ammonium compounds, are dispersed in water or water/alcohol mixtures together with the colorants, perfumes, hair-cosmetic active compounds and preservatives which are conventionally used.

The substances according to the invention can also be incorporated into cosmetic preparations for hair which are not rinsed out with water after use. This concerns, for example, hair tonics, which can contain about 0.05 to 0.1% of the oxypropylated quarternary ammonium compounds mentioned, or hair fixatives, wave sets in liquid, creme-form preparations, or as aerosols containing about 0.1 to 1% of these compounds.

In principle, it is also possible to use the substances according to the invention for the preparation of cosmetic emulsions for skin care. Through the substantive character of the substances, improved skin feel is achieved after use and, simultaneously, a stabilizing action in the finished preparations is achieved due to the emulsifying action.

The use of the oxypropylated quarternary ammonium compounds is illustrated further in the examples below. Unless otherwise stated, all quantities refer to the weight.

EXAMPLE 1

Hair rinses 3.0% of distearylmethylpoly-(oxypropyl)$_{2-3}$ammonium lactate
1.5% of cetyl/stearyl alcohol+3 moles of ethylene oxide
3.0% of cetyl alcohol
0.3% of perfume oil
water to 100%

EXAMPLE 2

Hair treatment agent without thickener 3.0% of distearylmethylpoly(oxypropyl)$_{2-3}$ammonium lactate
0.2% of perfume oil
water to 100%

EXAMPLE 3

Wave set 0.2% of distearylmethylpoly(oxypropyl)$_{2-3}$ammonium lactate
15% of isopropyl alcohol
0.2% of polyvinylpyrrolidone
0.1% of perfume oil
water to 100%

EXAMPLE 4

Hair after-treatment agent 2.0% of distearylmethylpoly(oxypropyl)$_{2-3}$ammonium lactate
1.0% of pentaoxyethylammonium lactate
3.5% of cetyl alcohol
water to 100%

EXAMPLE 5

Hair rinse 2.5% of distearylmethylpoly(oxypropyl)$_{2-3}$ammonium lactate
0.5% of behenyltrimethylammonium chloride
3.0% of cetyl alcohol
water to 100%

EXAMPLE 6

Hair after-treatment agent in aerosol form 0.1% of distearylmethylpoly(oxypropyl)$_{2-3}$ammonium lactate
0.1% of.cetyltrimethylammonium bromide
0.7% of cetyl/stearyl alcohol
water to 100%

The above mixture is transferred in a known fashion into aerosol containers along with a propellant.

EXAMPLE 7

Liquid skin-care agent 1.0% of distearylmethylpoly(oxypropyl)$_{2-3}$ammonium lactate
3.0% of tetraethylene glycol polyglyceryl distearate
10.0% of paraffin oil
10.0% of isopropyl palmitate
0.1% of perfume oil
water to 100%

EXAMPLE 8

Skin-care agent in creme form 2.0% of distearylmethylpoly(oxypropyl)$_{2-3}$ammonium lactate
6.0% of tetraethylene glycol polyglyceryl distearate
15.0% of paraffin oil 5.0% of isopropyl myristate
water to 100%

We claim:

1. An agent for treatment of hair and skin, containing a quarternary ammonium compound of the formula $$\left[ \begin{array}{c} R_1 \\ \diagdown \\ N^{\oplus} \\ \diagup \\ R_2 \end{array} \begin{array}{c} R_3 \\ \diagdown \\ CH_3 \\ | \\ (CH_2CHO)_xH \end{array} \right] A^{\ominus}$$

in which $R_1$ and $R_2$ may be identical or different and denote $C_8$–$C_{22}$-alkyl or $C_8$–$C_{22}$-alkenyl, $R_3$ denotes $C_1$–$C_3$-alkyl, x denotes a number from 1 to 3 and $A^{\ominus}$ denotes the anion of a $C_2$–$C_6$-carboxylic acid which may contain 1 to 3 hydroxyl groups, or the hydrogen phosphate anion.

2. An agent as claimed in claim 1 for treatment of hair, containing a quarternary ammonium compound of the formula specified, where $R_1$ and $R_2$ denote $C_{12}$–$C_{18}$-alkyl, $R_3$ denotes methyl, x denotes a number from 1.5 to 2.5, and $A^{\ominus}$ denotes the anion of lactic acid, citric acid or tartaric acid.

3. An agent for treatment of hair and skin, comprising:

(a) a quaternary ammonium compound of the formula $$\left[ \begin{array}{c} R_1 \\ \diagdown \\ N^{\oplus} \\ \diagup \\ R_2 \end{array} \begin{array}{c} R_3 \\ \diagdown \\ CH_3 \\ | \\ (CH_2CHO)_xH \end{array} \right] A^{\ominus}$$

in which $R_1$ and $R_2$ are identical or different and denote $C_8$–$C_{22}$ alkyl, $R_3$ denotes $C_1$–$C_3$ alkyl, x denotes a number from 1 to 3 and $A^{\ominus}$ denotes the anion of a $C_2$–$C_6$ carboxylic acid containing 1 to 3 hydroxyl groups, or the hydrogen phosphate anion; and (b) an ingredient which is at least one of the following: a thickener, a fat component, a preservative, a perfume oil, a colorant, a light screen or an alcohol.

4. An agent as claimed in claim 3, wherein said ingredient is dispersed or emulsified in water or a water/alcohol mixture or dissolved in alcohol.

5. An agent as claimed in claim 4 wherein said ingredient is cosmetically active.

6. An agent as claimed in claim 5, wherein $A^{\ominus}$ denotes the anion of lactic acid, citric acid, or tartaric acid.

7. An agent as claimed in claim 3, wherein said agent contains water and wherein said ingredient is at least one of the following: cetyl alcohol, the reaction product of cetyl alcohol and ethylene oxide, stearyl alcohol, perfume oil, isopropyl alcohol, polyvinylpyrrolidone, an additional quaternary ammonium compound, paraffin oil, tetraethylene glycol polyglyceryl distearate, isopropyl palmitate, or isopropyl myristate.

8. An agent for the treatment of hair, consisting essentially of the following ingredients:

(a) 0.05–10% of a quaternary ammonium compound of the formula $$\left[ \begin{array}{c} R_1 \\ \diagdown \\ N^{\oplus} \\ \diagup \\ R_2 \end{array} \begin{array}{c} R_3 \\ \diagdown \\ CH_3 \\ | \\ (CH_2CHO)_xH \end{array} \right] A^{\ominus}$$

in which $R_1$ and $R_2$ are identical or different and denote $C_{12}$–$C_{18}$ alkyl, $R_3$ denotes methyl, x denotes a number from 1.5 to 2.5, and $A^{\ominus}$ denotes the anion of lactic acid, citric acid, or tartaric acid, and (b) an effective amount of at least one additional ingredient selected from the group consisting of a perfume, a thickener, a preservative, a colorant, or a hair-cosmetic active compound, and (c) water or a water/alcohol mixture, substantially to 100%.

* * * * *